United States Patent
Lev et al.

(10) Patent No.: US 8,290,243 B2
(45) Date of Patent: Oct. 16, 2012

(54) SYSTEM AND METHOD FOR INSPECTION

(75) Inventors: Michael Lev, Yokneam (IL); Menachem Regensburger, Shimshit (IL); Gilad Golan, Ra'anana (IL); Yacov Manilovich, Kiryat Tiovn (IL)

(73) Assignee: Camtek Ltd., Migdal Haemeq (IL)

( * ) Notice: Subject to any disclaimer, the term of this patent is extended or adjusted under 35 U.S.C. 154(b) by 420 days.

(21) Appl. No.: 12/693,866

(22) Filed: Jan. 26, 2010

(65) Prior Publication Data
US 2010/0245566 A1     Sep. 30, 2010

Related U.S. Application Data

(60) Provisional application No. 61/147,497, filed on Jan. 27, 2009.

(51) Int. Cl.
*G06K 9/00* (2006.01)

(52) U.S. Cl. .................. 382/149; 382/141; 382/145

(58) Field of Classification Search .................. None
See application file for complete search history.

(56) References Cited

U.S. PATENT DOCUMENTS
2009/0279776 A1 * 11/2009 Tirosh .......................... 382/149
* cited by examiner

*Primary Examiner* — Jason M Repko
*Assistant Examiner* — Siamak Harandi
(74) *Attorney, Agent, or Firm* — Reches Patents (57) ABSTRACT

Method and inspection system. The inspection system includes: (i) a stage, for supporting an inspected object and for moving the inspected object by a movement that is characterized by speed variations; (ii) a signal generator, for generating triggering pulses at a fixed frequency regardless of the speed variations; (iii) a stage location generator, for providing location information indicative of a location of the stage at points of time that are determined by the triggering pulses; (iv) a strobe illuminator for illuminating areas of the inspected object in response to the triggering pulses; (v) a camera for acquiring images of areas of the inspected object in response to the triggering pulses; wherein overlaps between the images of the areas of the inspected object are characterized by overlap variations; and (vi) a processor for associating location information to the acquired images.

17 Claims, 7 Drawing Sheets

SYSTEM AND METHOD FOR INSPECTION

CROSS-REFERENCE TO RELATED APPLICATIONS

This application claims the benefit of U.S. provisional Patent Application Ser. No. 61/147,497 filed Jan. 27, 2009 the entire contents of which are incorporated herein by reference.

BACKGROUND OF THE INVENTION

During inspection of an electrical circuit (like Printed Circuit Boards, semiconductor wafers, etc.), high resolution photography is used, for detection of defects. An electrical circuit is usually placed on a mechanical stage (hereinafter-stage), that moves in respect to a camera that obtains images of the electrical circuit.

Two major illumination schemes are known and include a continuous acquisition and illumination (e.g. using a line scan camera or a time-delay integration—TDI—camera), a snap-shot acquisition and flash illumination.

The flash illumination has to be synchronized to the camera snap-shot to prevent acquiring an at least partly black image (or at least a non well illuminated picture).

Also, it is usually required to know where the image has been captured relative to the moving stage. Prior art system stages include a stage encoder that issues a trigger upon an arrival of the stage to a desired location, respective to a location where an inspected circuit (or the stage itself) should be located for a proper image to be acquired.

Conveniently, such a trigger will trigger the flash and the camera for illumination and acquisition respectively. Also, it is noted that flash duration should usually be relatively short so the image will not be blurred during motion.

Figure 1:
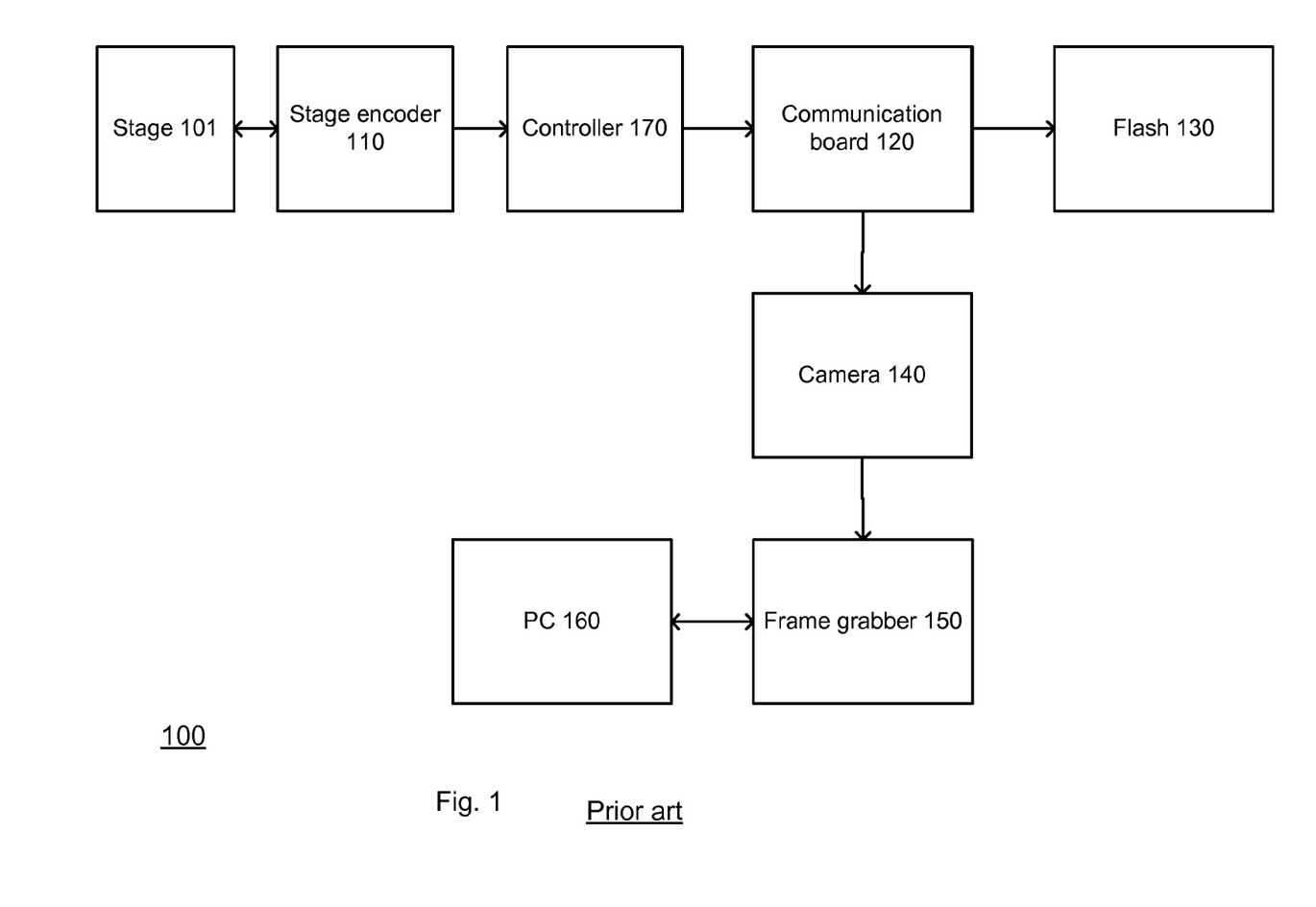
FIG. 1 illustrates a prior art system and various signals that are sent between components of the system.

FIG. 1 illustrates a prior art system 100 and various signals that are sent between components of the system 100.

System 100 includes stage 101, stage encoder 110, controller 170, distributer (also referred to as communication board 120), strobe illumination unit (such as flash 130), camera 140, frame grabber 150 and personal computer (PC) 160.

Stage 101 carries the electrical circuits to a designated direction (X-axis, Y-axis or both X-axis and Y-axis movement) at a speed that varies and is not maintained at a fixed value.

The camera 140 has a rectangular field of view (frame) that includes FOVx×FOVy pixels. FOVx is the number of pixels along the x-axis and FOVy is the number of pixels along the y-axis.

Stage encoder 110 is connected to stage 101 and issues a pulse (trigger) that is relative to a distance or a movement of the stage 10 (e.g. every FOVy*PIXEL_SIZEy, in microns). This stage movement based trigger activates the camera 140 to acquire images, and triggers the strobe illumination unit 130 to illuminate the electrical circuit.

The images which are captured by camera 140 in response to such triggering are transmitted to a frame grabber 150 and then are sent to PC 160 for image processing.

As indicated above, the frequency of the triggering signal (of a camera trigger and/or a flash trigger) is initiated by the position of the stage in different times.

Frame grabber 150 can acquire images at a fixed maximal rate. Temporal speed increments of stage 101 can temporarily increase the provision rate of images by frame grabber 150 as stage 101 passes the distance of FOVy*PIXEL_SIZEy more quickly. In order to manage these temporal speed increments, stage 101 should move the electrical circuit at a speed that is lower than an optimal speed.

In addition, system 100 must acquire images while maintaining a fixed overlap between consecutive images of areas of the electrical circuit. This demand requires system 100 to impose strict limitation on the speed of stage 101 and move stage 101 slower than maximal speed to provide better controllability.

Figure 2:
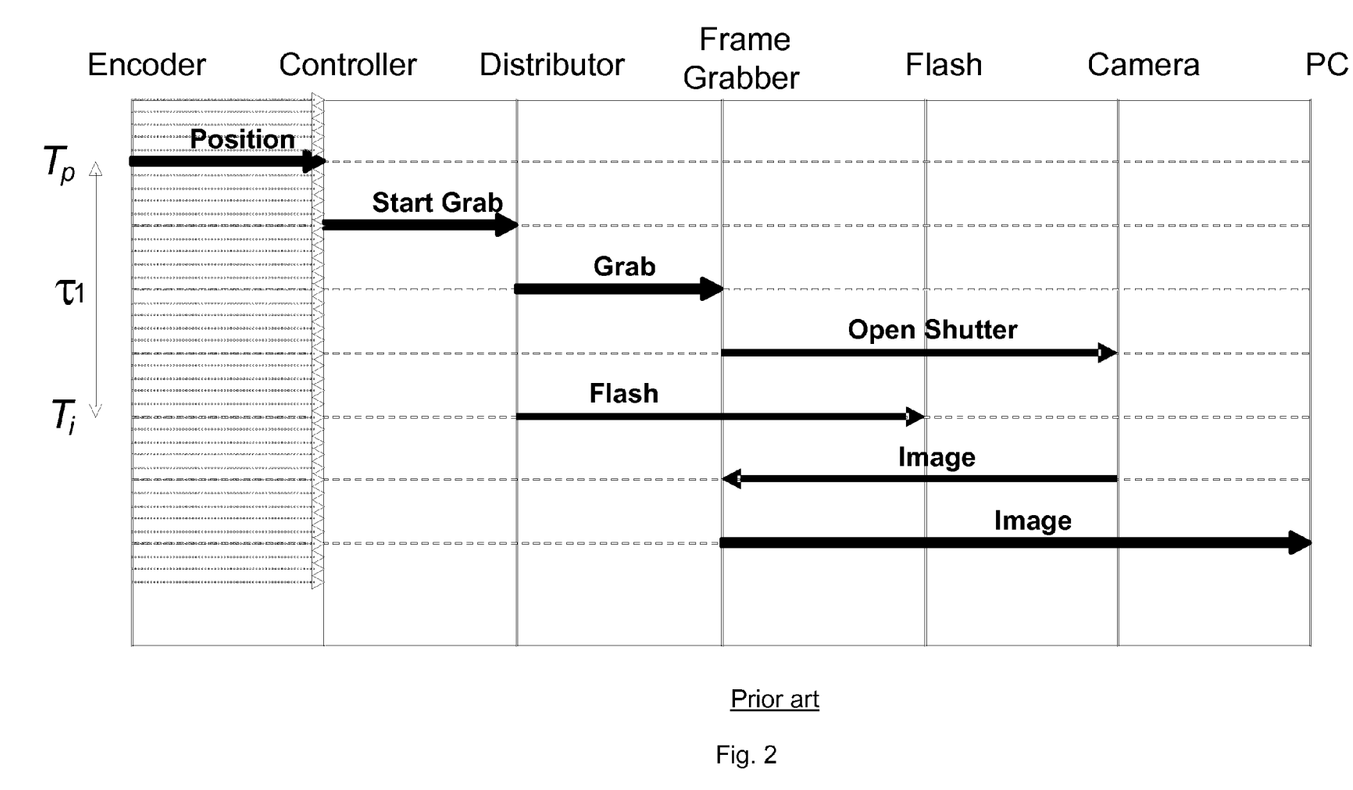
FIG. 2 illustrates the signals that are being exchanged between the components of the system of FIG. 1.

FIG. 2 illustrates the signals that are being exchanged between the components of system 100.

At time $T_p$ stage encoder 110 sends a triggering signal "position" that is responsive to the location of stage 101 on which an inspected electrical circuit is placed. The "position" triggering signal is sent to controller 170 that, in response, sends a "start grab" triggering signal to distributer 120. The distributer 120 sends a "grab" triggering signal to frame grabber 150 and sends a "flash" triggering signal to strobe illumination unit 130. The "flash" triggering signal is sent in a delay $\tau_1$ after Tp. Frame grabber 150 receives the "grab" triggering signal and sends an "open shutter" triggering signal to camera 140.

The "grab" triggering signal is sent to frame grabber 150 before the "open shutter" triggering signal is sent to camera 140. The "open shutter" signal precedes the "flash" triggering signal that is sent to the strobe illumination unit 130.

The "open shutter" triggering signal causes camera 140 to obtain an image and send it (as indicated by the "image" arrow) to frame grabber 150. Frame grabber 150 sends the image to computer 160.

The duration $\tau_1$ which is the latency between the time that the stage is in a known position and the time in which the strobe flashes could usually be calibrated, but the flashing of the flash/strobe in the prior art inspection is substantially triggered by a location of the stage.

SUMMARY OF EMBODIMENTS OF THE INVENTION

An inspection system can be provided. The inspection system can include a stage, for supporting an inspected object and for moving the inspected object by a movement that is characterized by speed variations; a signal generator, for generating triggering pulses at a fixed frequency regardless of the speed variations; a stage location generator, for providing location information indicative of a location of the stage at points of time that are determined by the triggering pulses; a strobe illuminator for illuminating areas of the inspected object in response to the triggering pulses; a camera for acquiring images of areas of the inspected object in response to the triggering pulses; wherein overlaps between the images of the areas of the inspected object are characterized by overlap variations; and a processor for associating location information to the acquired images.

The processor can compensate for the overlap variations—it can process pixels of an overlap area between two adjacent images based on the overlap between these two images even when the size of the overlap area changes between one pair of images to another.

The stage can be configured to reverse a direction of movement of the inspected object by a gradual change of direction of movement along each axis out of two axes.

The stage can be configured to move the inspected object according to a curved pattern.

The stage can be configured to move the inspected object without stopping a movement of the inspected object according to a hybrid pattern that comprises linear portions and curved portions.

The system can be configured to obtain images at a maximal throughput regardless of the speed variations.

The inspection system can include a distribution module for receiving the triggering signals, and generating camera triggering signals, frame grabber triggering signals and stage location triggering signals that are responsive to timing differences between propagation periods of the camera triggering signals, the frame grabber triggering signals and the stage location triggering signals.

The inspection system can include multiple strobe illuminators, and can be configured to switch between the different strobe illuminators. The different strobe illuminators can differ from each other by at least one illumination characteristic including but not limited to their location in relation to the inspected object.

The inspection system can change illumination characteristics such as color of light, length of strobe, phase of illumination, angle of illumination, numerical aperture of illumination, type of illumination (bright field, dark field) and the like. The change can occur while the stage is moving, during a scan, betweens scans and the like.

A method can be provided. The method can include: supporting, by a stage, an inspected object and moving the inspected object by a movement that is characterized by speed variations; generating triggering pulses at a fixed frequency regardless of the speed variations; providing location information indicative of a location of the stage at points of time that are determined by the triggering pulses; illuminating areas of the inspected object in response to the triggering pulses; acquiring, by a camera, images of areas of the inspected object in response to the triggering pulses; wherein overlaps between the images of the areas of the inspected object are characterized by overlap variations; and associating location information to the acquired images.

The method can include compensating for the overlap variations.

The method can include interpolating, based on the location information, locations of the stage when the images of the areas of the inspected object are acquired.

The method can include reversing a direction of movement of the inspected object by a gradual change of direction of movement along each axis out of two axes.

The method can include moving the inspected object according to a curved pattern.

The method can include moving the inspected object without stopping a movement of the inspected object according to a hybrid pattern that comprises linear portions and curved portions.

The method can include operating a frame gabber at a maximal throughput regardless of the speed variations.

The method can include receiving the triggering signals, and generating camera triggering signals, frame grabber triggering signals and stage location triggering signals that are responsive to timing differences between propagation periods of the camera triggering signals, the frame grabber triggering signals and the stage location triggering signals.

The method can include switching between the different strobe illuminators.

The method can include changing illumination characteristics.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanied drawings in which:

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION OF EMBODIMENTS OF THE INVENTION

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Figure 3:
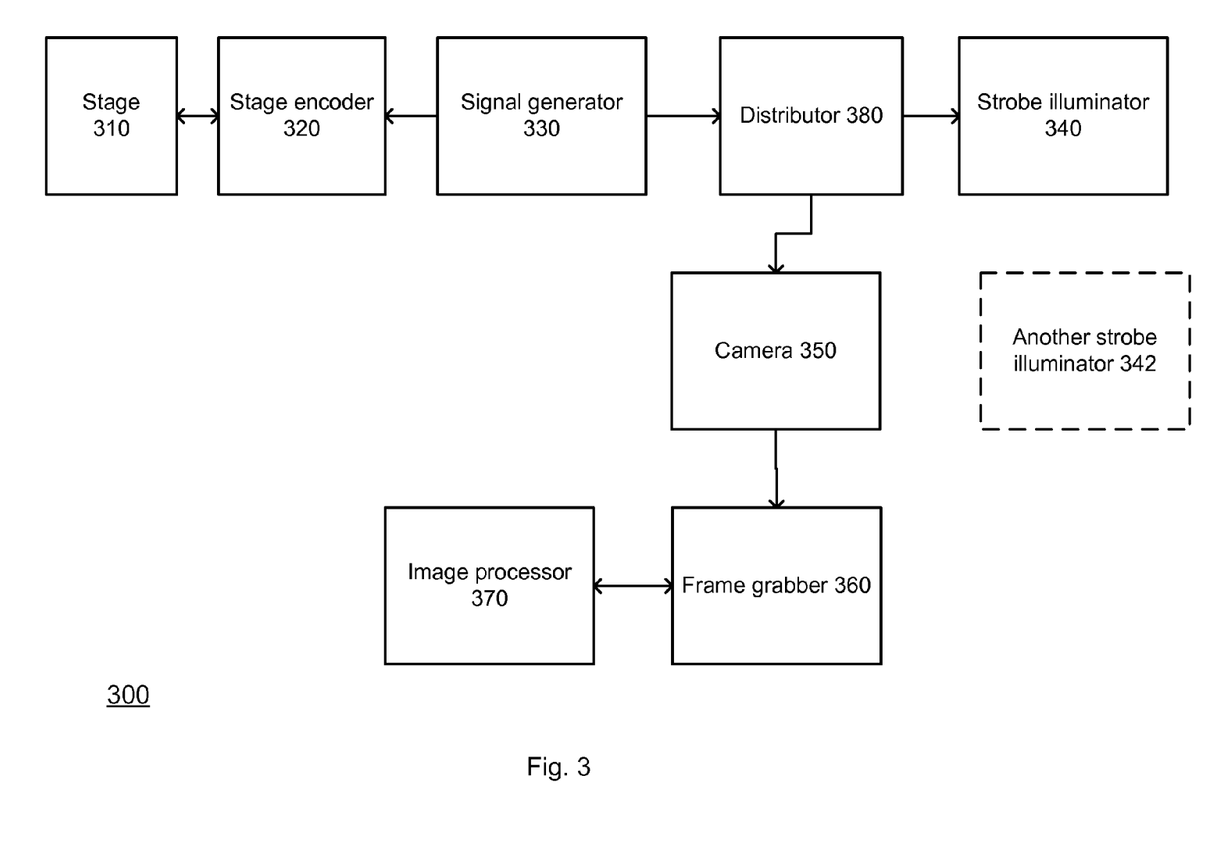
FIG. 3 illustrates an inspection system according to an embodiment of the invention.

FIG. 3 illustrates an inspection system 300 according to an embodiment of the invention.

System 300 includes: (i) stage 310, for supporting an inspected object and for moving the inspected object by a movement that is characterized by speed variations; (ii) signal generator 330, for generating triggering pulses at a fixed frequency regardless of the speed variations of stage 310; (iii) stage location generator (such as stage encoder 320), for providing location information indicative of a location of stage 310 at points of time that are determined by the triggering pulses; (iv) strobe illuminator 340 for illuminating areas of the inspected object in response to the triggering pulses; (v) camera 350 for acquiring images of areas of the inspected object in response to the triggering pulses; wherein overlaps between the images of the areas of the inspected object are characterized by overlap variations; (vi) frame grabber 360, for obtaining acquired images from the camera and for associating location information to the acquired images; (vii) image processor 370 for compensating for the overlap variations; and (ix) distributor 380 for distributing triggering signals. The compensation includes stitching images or otherwise processing pairs of images that may differ from each other by their overlap (the overlap between one pair can differ from an overlap between another pair).

It is noted that the image processor 370 and the frame grabber 380 can be reviewed as a single processor, that portions of the image processor 370 can be spaced apart from portions of the frame grabber 380 and the like.

The amount of overlap between images (and especially consequently acquired images) is determined by location information associated with these images. Image processor 370 can ignore pixels of the overlap area from one image and take into account pixels of the overlap area from another image. Alternatively, image processor 370 can take into account pixels from both images that are located in the overlap area.

By obtaining images at fixed rate and allowing different overlaps between images, stage 310 can be allowed to exhibit speed variations and the control demands from stage 310 can be relaxed—thus simplifying the stage control scheme and reducing the cost of stage 310.

By obtaining images at a fixed rate, regardless of speed variations of stage 310, the frame grabber can be activated at a maximal rate—regardless of the speed variations—as changes in speed do not increase the number of pixels it is required to receive.

Conveniently, frame grabber 360 can receive location information from stage encoder 320 at certain points of time and calculate (for example—by interpolation) the locations of stage 310 when the images of the areas of the inspected object are acquired from location information generated by stage encoder 320.

Stage 310 can be allowed in a less accurate manner but at a higher speed. This can allow, replacing a rectangular raster scan pattern by a curved pattern in which the direction of stage 310 can be changed in a gradual manner, for example by performing a u-turn. Thus, stage 310 can be allowed to perform a gradual change of direction of movement along each axis out of two axes.

Figure 5:
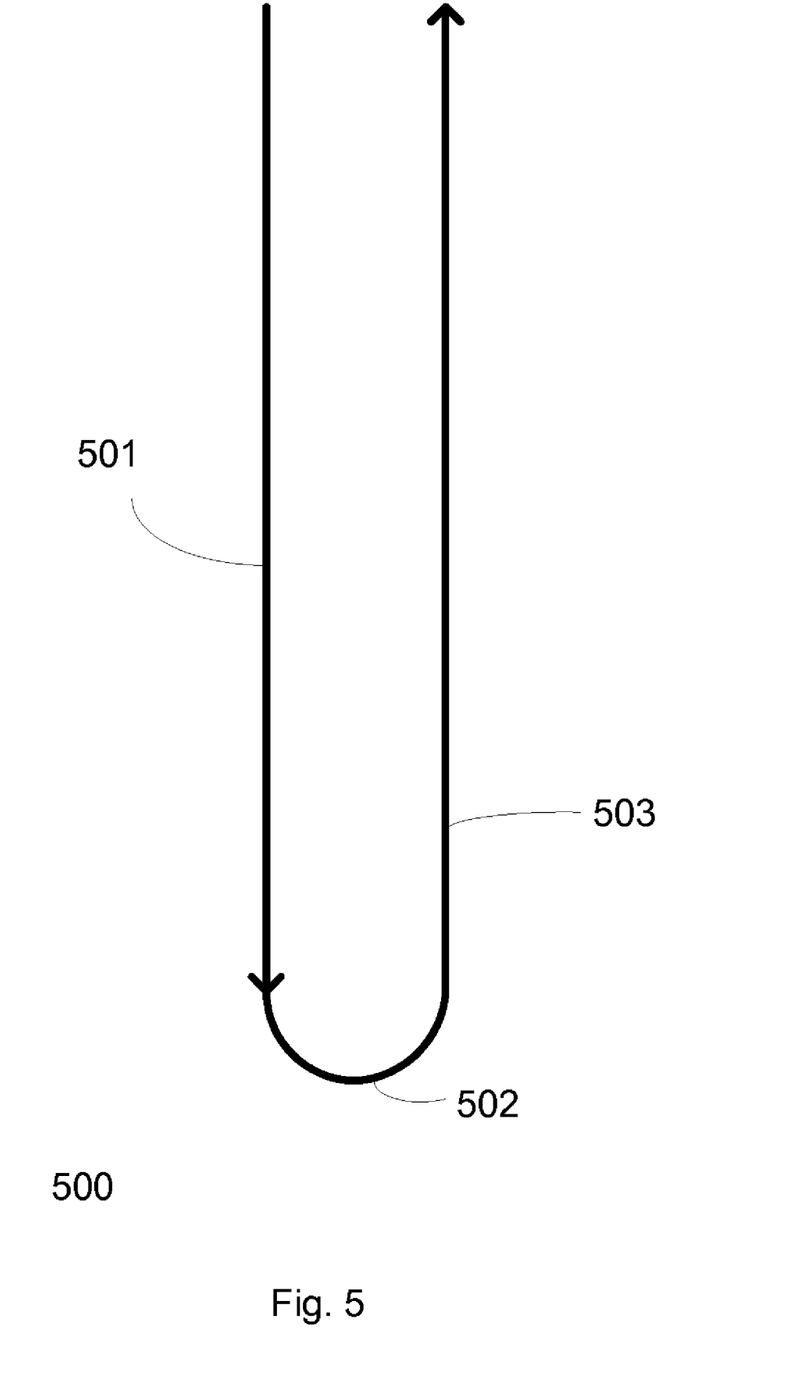
FIG. 5 illustrates a stage movement change according to an embodiment of the invention.

Stage 310 can be allowed to move the inspected object without stopping a movement of the inspected object according to a hybrid pattern that comprises linear portions and curved portions. An example of such pattern 500 is illustrated in FIG. 5. The stage moves along a first direction 501, performs a u-turn 502 and then moves along a second direction 503 that is opposite to the first direction 501.

Distributor 380 can receive triggering signals from signal generator 330 and generate camera triggering signals, frame grabber triggering signals and stage location triggering signals. These triggering signals can be delayed in relation to each other in order to compensate for timing differences between propagation periods of the camera triggering signals, the frame grabber triggering signals and the stage location triggering signals.

Signal generator 330 can be a clock that is configured to generate triggering pulses at a fixed rate that is determined regardless of the speed variations or the location of stage 310. The fixed rate can be determined based on a maximal throughput of frame grabber 360. The fixed rate can be determined by a user or operator based on a required quality of image, required illumination condition, and the like. The fixed rate can be determined so as to maximize and/or optimize a quality parameter—e.g. of strobe illuminator 340, of stage 310, of camera 350, of system 300 generally, and so forth.

Distributor 380 can provide synchronization tag to stage 310. It can include a delay line that delays different triggering signals (aimed to different components of system 300) by different delay periods.

Strobe illuminator 340 provides flashes on and off at the constant rate that is defined by the triggering signals provided by signal generator 330 and is independent from any other factor or correlation.

Different overlaps can be allowed to exist between consecutive images and the overlaps can be responsive not just to the speed variations of the stage but also responsive to a desired optical magnification.

System 300 can determine (e.g. by a reporting by stage encoder 320) a spatial position at the time of the acquisition of an image acquired by camera 350, in order to facilitate an easy calculation of this appropriated overlap. The location can also be estimated or interpolated from location information generated by stage encoder 320 at points of time that can be proximate to the time in which camera 350 acquired the images.

Camera 350 sends its acquired image to frame grabber 360 that can store the image, process the image, sends the image to an image processor 370 and the like. Image processor 370 can be a part of system 300 but can also be a stand alone system or otherwise not integrated in system 300.

Frame grabber 360 and, additionally or alternatively, image processor 370 receive location information related to the images. This location information can assist in registration, image stitching and the like.

Figure 4:
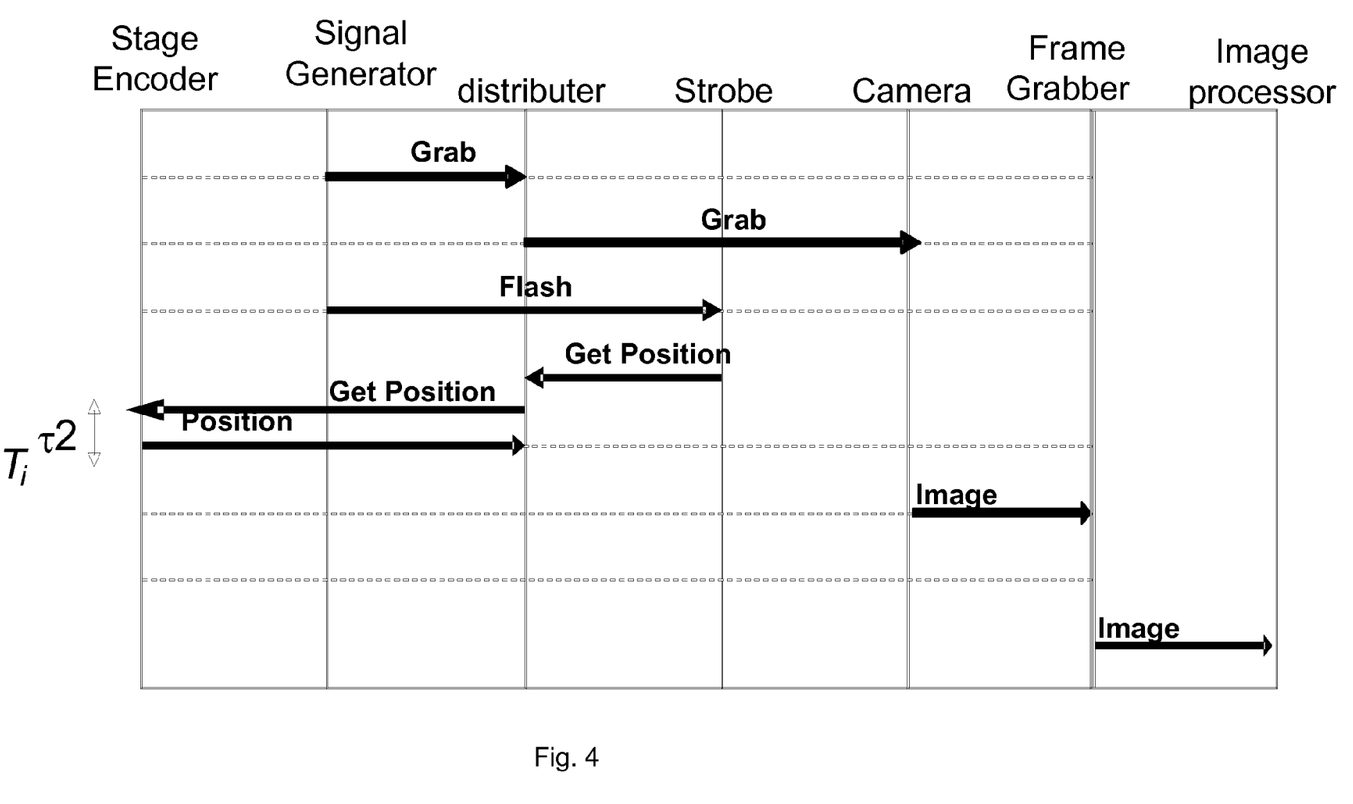
FIG. 4 illustrates signals that are being exchanged between the components of the system of FIG. 3.

FIG. 4 illustrates the signals that are being exchanged between the components of system 300.

Signal generator 330 can generate at a fixed rate and regardless of variations in the speed of stage 310, camera triggering signals, stage encoder triggering signals, strobe illuminator triggering signals and the like.

Alternatively, signal generator 330 can generate triggering signals that are converted to camera triggering signals, stage encoder triggering signals, strobe illuminator triggering signals (as well as other triggering signals) by distributor 380. The conversion can include introducing delays, reverse polarity and the like.

FIG. 4 illustrates the following sequence of events:
i. Signal generator 330 sends a triggering pulse ("grab") to distributor 380.
ii. The distributor 330 sends a camera triggering signal ("grab") to camera 350.
iii. The signal generator 330 sends a strobe illuminator triggering signal ("flash") to strobe illuminator 340.
iv. The strobe illuminator 340 sends stage encoder triggering signal ("get position"—requesting the location of stage 310 when strobe illuminator 340 flashes) to distributor 380. The stage encoder triggering signal is also referred to as positioning determination triggering.
v. Distributor 380 sends the stage encoder triggering signal to stage encoder 320.
vi. Stage encoder 320 provides location information about the stage at a point of time Ti. The time difference ($\tau_2$) between the flash and Ti can be known in advance.
vii. Camera 350 sends an acquired image to frame grabber 360 that in turn can send the image to image processor 370 or process one or more images and store it, or send a processed image (or images) to another entity.

In this sequence the instruction to grab the picture is not issued by stage encoder 320.

An instruction to grab an image (camera triggering signal) can be transmitted from signal generator 330 to frame grabber 360.

Conveniently, camera 350, that was triggered prior to the flashing, acquires the image when the strobe flashes. It is noted that a shutter of camera 350 may be opened for a longer period than the actual duration of the flashing.

The position of stage 310 at the time of flashing may be determined in response to timing information received from strobe illuminator 340, and may also be determined in response to timing information that is received from other modules such as signal generator 330 or frame grabber 360.

The positioning information is conveniently received from a component that is connected to stage 310, such as stage encoder 320.

It is noted that the image that is acquired by camera 350 is conveniently transferred from camera 350 to at least one system which can process and/or store those images (e.g. image processor 370 via frame grabber 360). The transmission of the image (and possibly also at least some of the acquiring of the image) may take place after the determination of the positioning information, but this is not necessarily so.

System 300 can include multiple strobe illuminators—as illustrated by strobe illuminator 340 and additional strobe illuminator 342. The system 300 can switch between strobe illuminators. The system 300 can alter illumination characteristics.

Especially, the disclosed invention facilitates an accurate and easy synchronization between strobe illuminator 340 and camera 350.

Significantly, the invention is especially suitable for "rolling shutter" cameras.

Also, it is noted that the position error on $T_i$ is conveniently determined as:

$$\tau \times \text{Velocity Ripple}$$

As it is clear to a person who is skilled in the art, $\tau_2 < \tau_1$. Moreover, as frame grabber 350 gets repeatable readings of the position—if the latency of system 300 ($\tau_2$) it can be used to calculate the position in which stage 310 was exactly at the time of the flash. This may some or all of the following effects:

i. Ease the demands from stage 310.
ii. Result in a more accurate position.
iii. Reduce the control requirements.

That is, by offering a system and a method in which the triggering of the imaging and of the flash does not require a determination of the location of the stage, and which is not responsive thereto, more accurate a determination of the location in which an image was taken is disclosed, as well as simpler control requirements.

Figure 6:
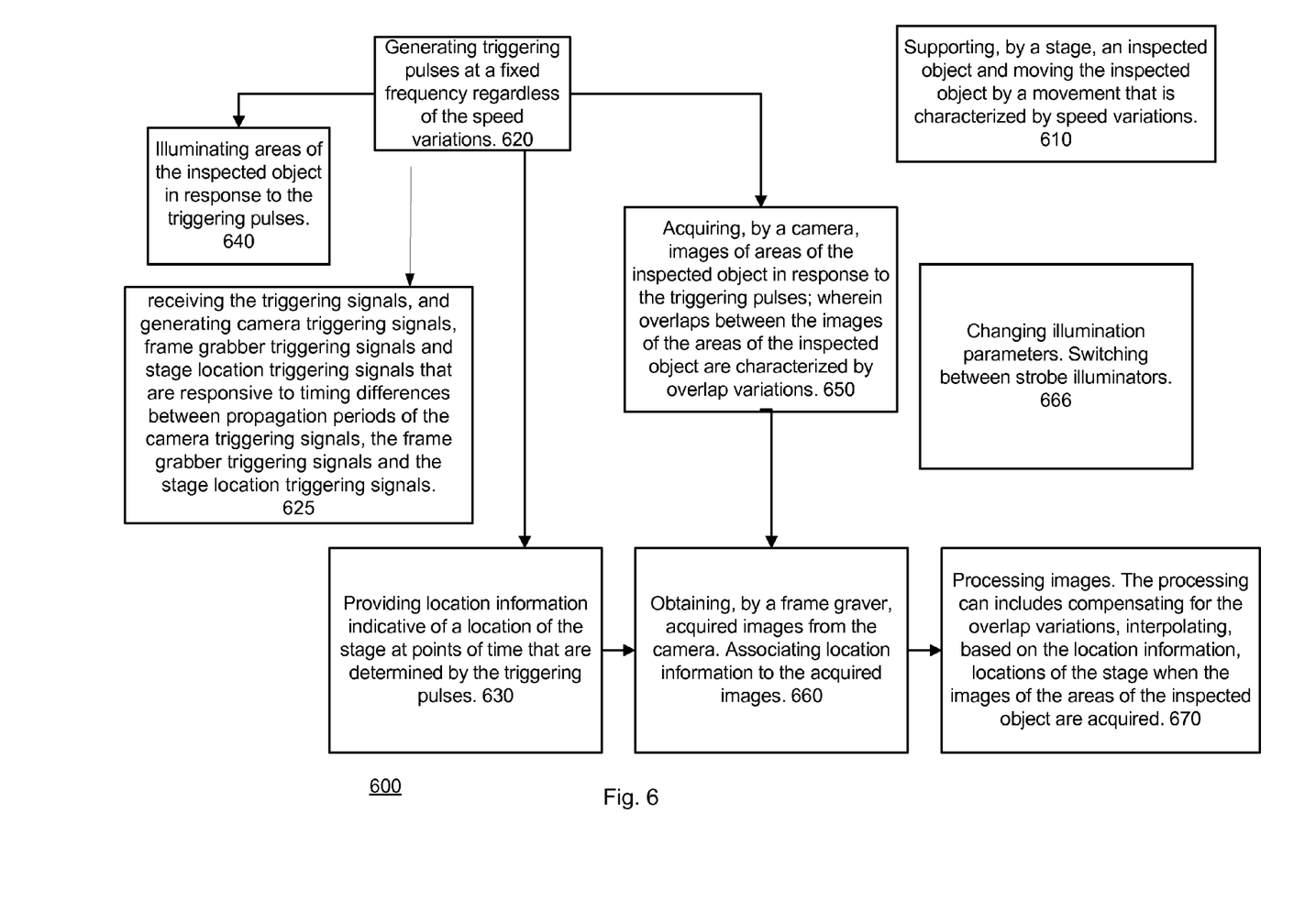
FIG. 6 illustrates a method according to an embodiment of the invention.

FIG. 6 illustrates a method 600 according to an embodiment of the invention.

Method 600 may include stages 610-670.

Stage 610 includes supporting, by a stage, an inspected object and moving the inspected object by a movement that is characterized by speed variations.

Stage 620 includes generating triggering pulses at a fixed frequency regardless of the speed variations.

Stage 630 includes providing location information indicative of a location of the stage at points of time that are determined by the triggering pulses.

Stage 640 includes illuminating areas of the inspected object in response to the triggering pulses.

Stage 650 includes acquiring, by a camera, images of areas of the inspected object in response to the triggering pulses; wherein overlaps between the images of the areas of the inspected object are characterized by overlap variations.

Stage 660 includes obtaining, by a frame graver, acquired images from the camera and associating location information to the acquired images.

Stage 670 includes processing images. Stage 670 can include: (i) compensating for the overlap variations, (ii) interpolating, based on the location information, locations of the stage when the images of the areas of the inspected object are acquired.

Stage 610 can include reversing a direction of movement of the inspected object by a gradual change of direction of movement along each axis out of two axes.

Stage 610 can include moving the inspected object according to a curved pattern.

Stage 610 can include moving the inspected object without stopping a movement of the inspected object according to a hybrid pattern that comprises linear portions and curved portions.

Stage 660 can include operating a frame gabber at a maximal throughput regardless of the speed variations.

Stage 620 can be followed by stage 625 of receiving the triggering signals, and generating camera triggering signals, frame grabber triggering signals and stage location triggering signals that are responsive to timing differences between propagation periods of the camera triggering signals, the frame grabber triggering signals and the stage location triggering signals.

Method 600 can include stage 666 of changing illumination parameters. Stage 666 may include switching between strobe illuminators.

Figure 7:
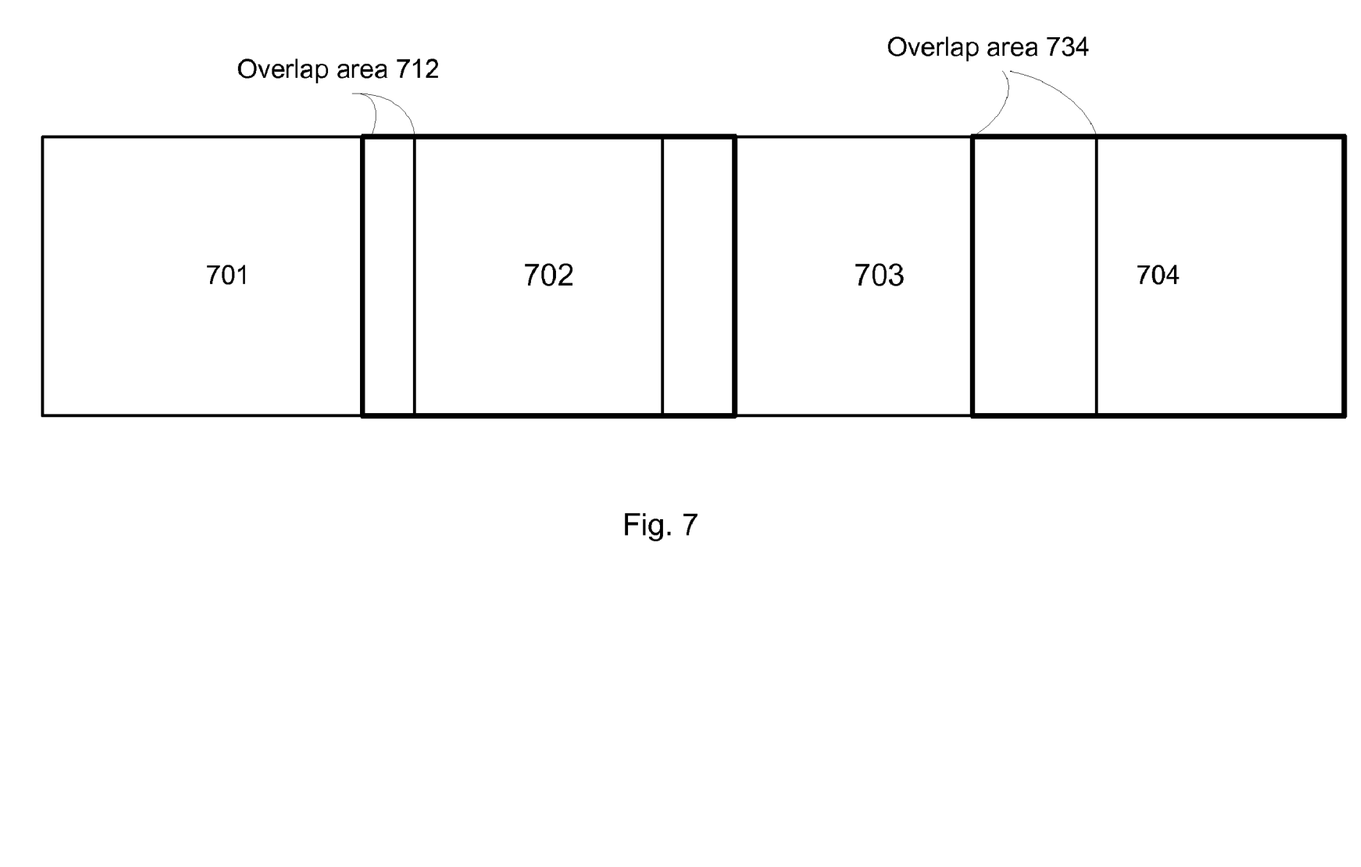
FIG. 7 illustrates various images according to an embodiment of the inventor.

FIG. 7 illustrates various images 701, 702, 703 and 704 according to an embodiment of the inventor.

Due to the speed variations and due to the sequential acquisition (fixe rate) of images 701-704 the size of the overlap area differs between consecutive images. Thus, a size of overlap area 712 between images 701 and 702 differs from a size of overlap area 734 between images 703 and 704.

The processor receives location information and can calculate from the location information (especially—fro the difference between location information associated with different images) the size of the overlap area. This can assist the processor in processing pixels from different images. For example, the size of the overlap can assist the processor in stitching images together, and the like. The boundaries of the overlap area defined the pixels that belong to both images and those who belong only to a single image.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An inspection system, comprising:
   a stage, for supporting an inspected object and for moving the inspected object by a movement that is characterized by speed variations;
   a signal generator, for generating triggering pulses at a fixed frequency regardless of the speed variations;
   a stage location generator, for providing location information indicative of a location of the stage at points of time that are determined by the triggering pulses;
   a strobe illuminator for illuminating areas of the inspected object in response to the triggering pulses;
   a camera for acquiring images of areas of the inspected object in response to the triggering pulses;

a processor for associating location information to the acquired images; and a distribution module for receiving the triggering pulses, and generating camera triggering signals, frame grabber triggering signals and stage location triggering signals that are responsive to timing differences between propagation periods of the camera triggering signals, the frame grabber triggering signals and the stage location triggering signals.

2. The inspection system according to claim 1, wherein the processor is configured to compensate for the overlap variations.

3. The inspection system according to claim 1, wherein the stage is configured to reverse a direction of movement of the inspected object by a gradual change of direction of movement along each axis out of two axes.

4. The inspection system according to claim 1, wherein the stage is configured to move the inspected object according to a curved pattern.

5. The inspection system according to claim 1, wherein the stage is configured to move the inspected object without stopping a movement of the inspected object according to a hybrid pattern that comprises linear portions and curved portions.

6. The inspection system according to claim 1 adapted to obtain images at a maximal throughput regardless of the speed variations.

7. The inspection system according to claim 1, comprising multiple strobe illuminators, and wherein the system is adapted to switch between the different strobe illuminators.

8. The inspection system according to claim 1, wherein the system is adapted to change illumination characteristics.

9. A method, comprising:

supporting, by a stage, an inspected object and moving the inspected object by a movement that is characterized by speed variations;

generating triggering pulses at a fixed frequency regardless of the speed variations;

receiving the triggering pulses and generating camera triggering signals, frame grabber triggering signals and stage location triggering signals that are responsive to timing differences between propagation periods of the camera triggering signals, the frame grabber triggering signals and the stage location triggering signals;

providing location information indicative of a location of the stage at points of time that are determined by the triggering pulses;

illuminating areas of the inspected object in response to the triggering pulses;

acquiring, by a camera, images of areas of the inspected object in response to the triggering pulses; wherein overlaps between the images of the areas of the inspected object are characterized by overlap variations; and associating location information to the acquired images of the areas of the inspected object.

10. The method according to claim 9, comprising compensating for the overlap variations.

11. The method according to claim 9, comprising interpolating, based on the location information, locations of the stage when the images of the areas of the inspected object are acquired.

12. The method according to claim 9, comprising reversing a direction of movement of the inspected object by a gradual change of direction of movement along each axis out of two axes.

13. The method according to claim 9, comprising moving the inspected object according to a curved pattern.

14. The method according to claim 9, comprising moving the inspected object without stopping a movement of the inspected object according to a hybrid pattern that comprises linear portions and curved portions.

15. The method according to claim 9, comprising obtaining images at a maximal throughput regardless of the speed variations.

16. The method according to claim 9, comprising switching between different strobe illuminators.

17. The method according to claim 9, comprising changing illumination characteristics.

* * * * *